(12) United States Patent
Wang

(10) Patent No.: US 9,797,828 B2
(45) Date of Patent: Oct. 24, 2017

(54) METHOD FOR MEASURING THE CONCENTRATION OF A PHOTORESIST IN A STRIPPING LIQUID

(71) Applicant: SHENZHEN CHINA STAR OPTOELECTRONICS TECHNOLOGY CO., LTD., Shenzhen, Guangdong (CN)

(72) Inventor: Li Wang, Guangdong (CN)

(73) Assignee: SHENZHEN CHINA STAR OPTOELECTRONICS TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 14/647,100

(22) PCT Filed: May 23, 2014

(86) PCT No.: PCT/CN2014/078266
§ 371 (c)(1),
(2) Date: May 25, 2015

(87) PCT Pub. No.: WO2015/143768
PCT Pub. Date: Oct. 1, 2015

(65) Prior Publication Data
US 2017/0003216 A1    Jan. 5, 2017

(30) Foreign Application Priority Data
Mar. 27, 2014  (CN) .......................... 2014 1 0118203

(51) Int. Cl.
*G01J 3/00*  (2006.01)
*G01N 21/33*  (2006.01)
(Continued)

(52) U.S. Cl.
CPC ............... *G01N 21/33* (2013.01); *G01N 1/38* (2013.01); *G01N 2021/3155* (2013.01); *G01N 2201/13* (2013.01)

(58) Field of Classification Search
CPC ........ G01N 21/33; G01N 1/38; G01N 21/359; G01N 2021/3155; A61K 39/095;
(Continued)

(56) References Cited

U.S. PATENT DOCUMENTS

2003/0138710 A1*  7/2003  Park ..................... G01N 21/359
                                                           430/30
2010/0253934 A1* 10/2010  D'Ascenzi ........... A61K 39/095
                                                           356/51

FOREIGN PATENT DOCUMENTS

CN         1439120 A      8/2003
CN       102435547 A      5/2012
JP       H06331541 A     12/1994

OTHER PUBLICATIONS

Hailing Wang, the International Searching Authority written comments, Oct. 2014, CN.
(Continued)

*Primary Examiner* — Jamil Ahmed

(57) ABSTRACT

The present invention discloses a method for measuring the concentration of a photoresist in a stripping liquid. In the method for measuring the concentration of a photoresist in a stripping liquid, a plurality of standard photoresist samples are prepared at first, then the spectrum of the standard photoresist samples and the spectrum of the test photoresist sample are collected, and the nth derivative of the spectrum of the standard photoresist samples and the spectrum of the test photoresist sample are taken, wherein n is an integer equal to or greater than 1, a standard curve based on the nth derivative curves and calculating the concentration of the test photoresist sample is established, the concentration of a
(Continued)

photoresist in a stripping liquid can be measured accurately according to the standard curve.

11 Claims, 5 Drawing Sheets

(51) Int. Cl.
    *G01N 1/38* (2006.01)
    *G01N 21/31* (2006.01)
(58) Field of Classification Search
    CPC ........ G01M 2201/13; G03F 7/42; C23F 1/00; G01J 3/28; G01J 3/00
    See application file for complete search history.

(56) References Cited

OTHER PUBLICATIONS

Jian Guo, Ruizhong Ma, Ping Li, et al., Determination of Cyclosporine in Blood by Derivative Spectrophoyometry., Mar. 1996.vol. 18,No. 3,203-205,Journal of Weifang Medical College,CN.
Yuzhu Hu., Stoichiometric Introductory Tutorial., Oct. 1997,156-160,China Medical Science Press, CN.
Hongci Gao,etc. Practical Pharmacy Calculation.,Mar. 2007,159-161,Chemical Industry Press,CN.
Dongguang Li,Industrial Detergent Fosrmulation and Preparation,Aug. 2009,128, ChinaTextile & Apparel Press, CN.
Minbo Tian,TFT LCD Panel Design and Architecture Technology,Mar. 2010.115/134,139-140,Science Press ,CN.
Yangzhi Jin,Light Curing Material Performance and Application Manual.,Jul. 2010. 398.Chemicai Industry Press, CN.
Miaogen Qian, Modem Surface Engineering.,Sep. 2012,424-426,Profile of Shanghai Jiao Tong University Press,CN.
Li Meirong,Yuan Cunguang, Derivative Spectrophotometry for the determination of phenols and aromatic amines in sewage with extraction-reextradion,Dec. 1998,18(5):428-429,Journal of China Environmental Science,CN.
Ergang Zhao,Thin Layer Chromatography—Derivative Spectrophotometry for the Determination of the Content of Trinitrotoluene,Dec. 1998,No. 3:44-45,Journal of the Guangdong Public Security Science and Technology,CN.

* cited by examiner

METHOD FOR MEASURING THE CONCENTRATION OF A PHOTORESIST IN A STRIPPING LIQUID

FIELD OF THE INVENTION

The present invention relates to a method for measuring the concentration of a photoresist in a stripping liquid.

BACKGROUND OF THE INVENTION

Photoresist (PR) is widely used as mask patterns for form layers in TFT technologies. There are two types photoresist, i.e. positive photoresist and negative photoresist. When exposed, the exposed areas of the positive photoresist are made to be solvable in a developer, and the unexposed areas are left as a pattern.

The concentration of a photoresist in a stripping liquid (also be called as stripper) is usually measured by UV-VIS (Ultraviolet and Visible Spectrophotometer). In this method, the absorbance are read directly and stored in a database to measure the concentration of a photoresist in a stripping liquid. In this method, the operation is complicated and it is not suitable to put into practice.

SUMMARY OF THE INVENTION

The present invention provides a method for measuring the concentration of a photoresist in a stripping liquid, which can measure the concentration of a photoresist in a stripping liquid accurately.

The present invention is realized in such a way that: A method for measuring the concentration of a photoresist in a stripping liquid, the method for measuring the concentration of a photoresist in a stripping liquid comprising the steps of:

S102: preparing standard photoresist samples;
S104: collecting the spectrum of the standard photoresist samples and the spectrum of the test photoresist sample; and
S106: taking the nth derivative of the spectrum of the standard photoresist samples and the spectrum of the test photoresist sample, wherein n is an integer equal to or greater than 1, and storing the nth derivative curves of the nth derivative of the spectrum of the standard photoresist samples and the spectrum of the test photoresist sample;
S108: establishing a standard curve based on the nth derivative curves and calculating the concentration of the test photoresist sample.

Preferably, in step S102, photoresist is coated on a glass, an exposure process, a developing process and an etching process are performed, and a stripping process is simulated in a beaker by stripping the photoresist with a target weight, such as to obtain the standard photoresist samples with target concentrations.

Preferably, in step S104, the spectrum of the standard photoresist samples and the spectrum of the test photoresist sample are collected by ultraviolet and visible spectrophotometer.

Preferably, the step S104 comprises the steps of:
solvent preparing step: selecting a solvent as the reference solution;
the spectrum of the stripping liquid collecting step: diluting the stripping liquid with the reference solution, collecting the spectrum of the stripping liquid in the predetermined wavelength;
the spectrum of the standard photoresist samples collecting step: diluting a plurality of standard photoresist samples with the reference solution, collecting the spectrum of the plurality of standard photoresist samples in the predetermined wavelength;
the spectrum of the test photoresist sample collecting step: diluting the test photoresist sample with the reference solution, collecting the spectrum of the test photoresist sample in the predetermined wavelength.

Preferably, in step S106, taking the nth derivative of the spectrum of the stripping liquid, the spectrum of the standard photoresist samples and the spectrum of the test photoresist sample, wherein n is 1, 2, 3 or 4, and storing the nth derivative curves of the nth derivative of the spectrum of the stripping liquid, the spectrum of the standard photoresist samples and the spectrum of the test photoresist sample.

Preferably, in step S108, if the absorbance of the nth derivative curves of the nth derivative of the spectrum of the stripping liquid at a first wavelength is zero, and both the absorbance of the nth derivative curves of the nth derivative of the spectrum of the standard photoresist samples at the first wavelength and the absorbance of the nth derivative curves of the nth derivative of the spectrum of the test photoresist sample at the first wavelength are at respective troughs, then establishing the standard curve based on the respective troughs and the concentration of the photoresist of the standard photoresist samples.

Preferably, in step S108, if the absorbance of the nth derivative curves of the nth derivative of the spectrum of the stripping liquid at a second wavelength is zero, and both the absorbance of the nth derivative curves of the nth derivative of the spectrum of the standard photoresist samples at the second wavelength and the absorbance of the nth derivative curves of the nth derivative of the spectrum of the test photoresist sample at the second wavelength are at respective peaks, then establishing the standard curve based on the respective peaks and the concentration of the photoresist of the standard photoresist samples.

Preferably, in step S108, if the absorbance of the nth derivative curves of the nth derivative of the spectrum of the stripping liquid between a third wavelength and a fourth wavelength is zero, both the absorbance of the nth derivative curves of the nth derivative of the spectrum of the standard photoresist samples and the absorbance of the nth derivative curves of the nth derivative of the spectrum of the test photoresist samples at the third wavelength are at respective troughs, and both the absorbance of the nth derivative curves of the nth derivative of the spectrum of the standard photoresist samples and the absorbance of the nth derivative curves of the nth derivative of the spectrum of the test photoresist samples at the fourth wavelength are at respective peaks, then establishing the standard curve based on the difference of the absorbance between the third wavelength and the fourth wavelength and the concentration of the photoresist of the standard photoresist samples.

Preferably, the stripping liquid is organic amine stripping liquid.

Preferably, the photoresist is a phenolic resin positive type photoresist.

According to the present invention, in the method for measuring the concentration of a photoresist in a stripping liquid, a plurality of standard photoresist samples are prepared at first, then the spectrum of the standard photoresist samples and the spectrum of the test photoresist sample are collected, and the nth derivative of the spectrum of the standard photoresist samples and the spectrum of the test photoresist sample are taken, wherein n is an integer equal to or greater than 1, a standard curve based on the nth derivative curves and calculating the concentration of the test photoresist sample is established, the concentration of a photoresist in a stripping liquid can be measured accurately according to the standard curve.

For more clearly and easily understanding above content of the present invention, the following text will take a preferred embodiment of the present invention with reference to the accompanying drawings for detail description as follows.

BRIEF DESCRIPTION OF THE DRAWINGS

The drawings described herein are for illustration purposes only and are not intended to limit the scope of the present disclosure in any way.

DETAILED DESCRIPTION OF THE PREFERRED EMBODIMENTS

The embodiments of the present invention will be described in detail with reference to the accompanying drawings.

As shown in FIG. 1 to FIG. 5, the method for measuring the concentration of a photoresist in a stripping liquid in the present embodiment comprises the steps of:

S102: preparing standard photoresist samples;
S104: collecting the spectrum of the standard photoresist samples and the spectrum of the test photoresist sample; and
S106: taking the nth derivative of the spectrum of the standard photoresist samples and the spectrum of the test photoresist sample, wherein n is an integer equal to or greater than 1, and storing the nth derivative curves of the nth derivative of the spectrum of the standard photoresist samples and the spectrum of the test photoresist sample;
S108: establishing a standard curve based on the nth derivative curves and calculating the concentration of the test photoresist sample according to the standard curve.

In the present embodiment, the stripping liquid is organic amine stripping liquid. And the photoresist is a phenolic resin positive type photoresist.

Figure 1:
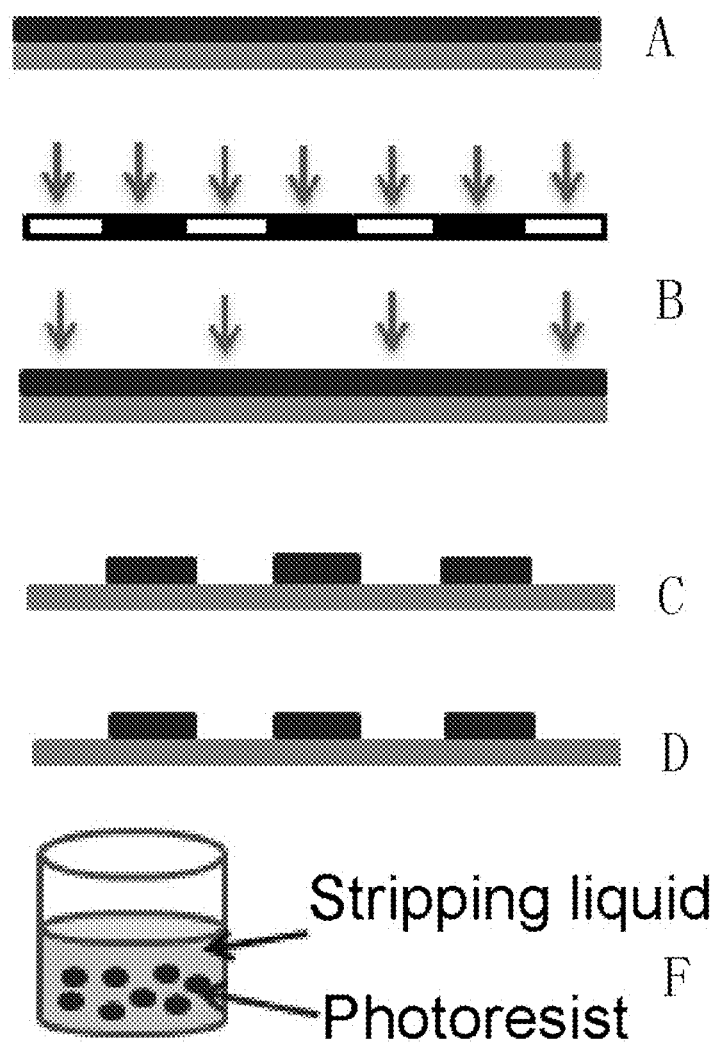
FIG. 1 is a schematic view illustrating the step of preparing standard photoresist samples according to an embodiment of the present invention.

As shown in FIG. 1, in step S102, photoresist is coated on a glass (step A), an exposure process (step B), a developing process (step C) and an etching process (step D) are performed, and a stripping process (step F) is simulated in a beaker by stripping the photoresist with a target weight, such as to obtain the standard photoresist samples with target concentrations. The difference between the step S102 and the practical photo lithography of TFT array process, metal layers and non-metal layers are not deposited on the glass in step S102.

In step S104, the spectrum of the standard photoresist samples and the spectrum of the test photoresist sample are collected by ultraviolet and visible spectrophotometer.

The step S104 comprises the steps of:

solvent preparing step: selecting a solvent as the reference solution, the solvent can be selected based on the dissolution performance, economic factor and safety factor;

baseline scanning step: scanning the reference solution in visible light region and ultraviolet light region;

the spectrum of the stripping liquid collecting step: diluting the stripping liquid with the reference solution, collecting the spectrum of the stripping liquid in the predetermined wavelength;

the spectrum of the standard photoresist samples collecting step: diluting a plurality of standard photoresist samples (3~5 standard photoresist samples for example) with the reference solution, collecting the spectrum of the plurality of standard photoresist samples in the predetermined wavelength;

the spectrum of the test photoresist sample collecting step: diluting the test photoresist sample with the reference solution, collecting the spectrum of the test photoresist sample in the predetermined wavelength.

Figure 2:
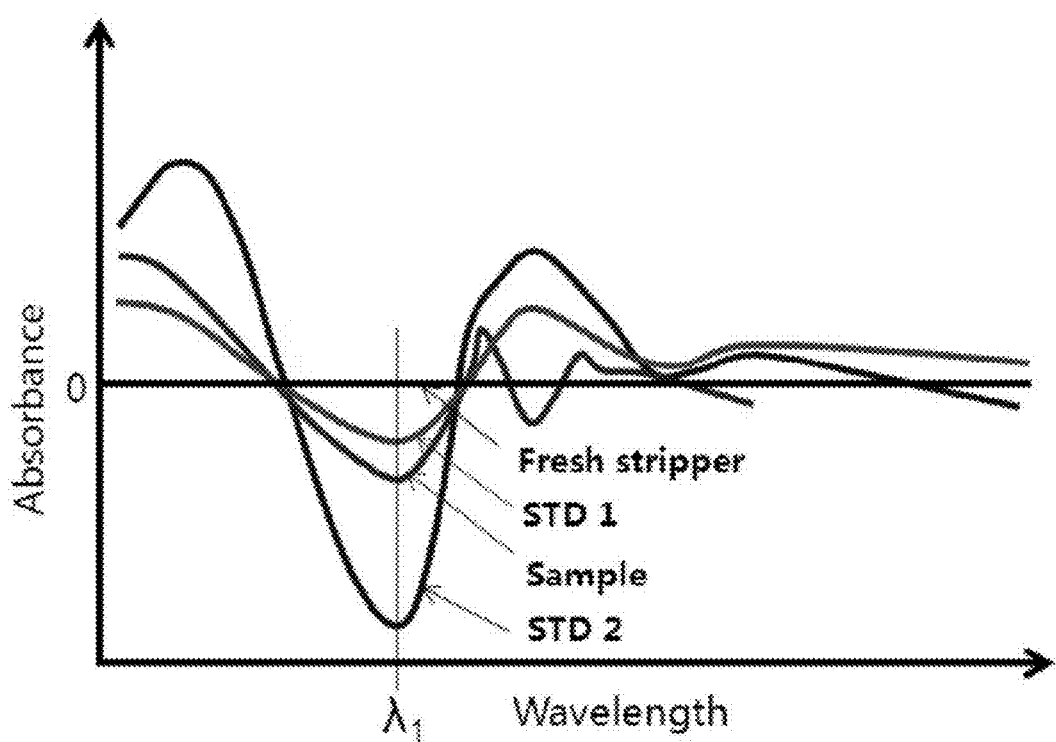
FIG. 2 is a schematic view illustrating that both the absorbance of the nth derivative curves of the nth derivative of the spectrum of the standard photoresist samples and the absorbance of the nth derivative curves of the nth derivative of the spectrum of the test photoresist sample at the first wavelength λ1 are at respective troughs in another embodiment of the present invention.
Figure 3:
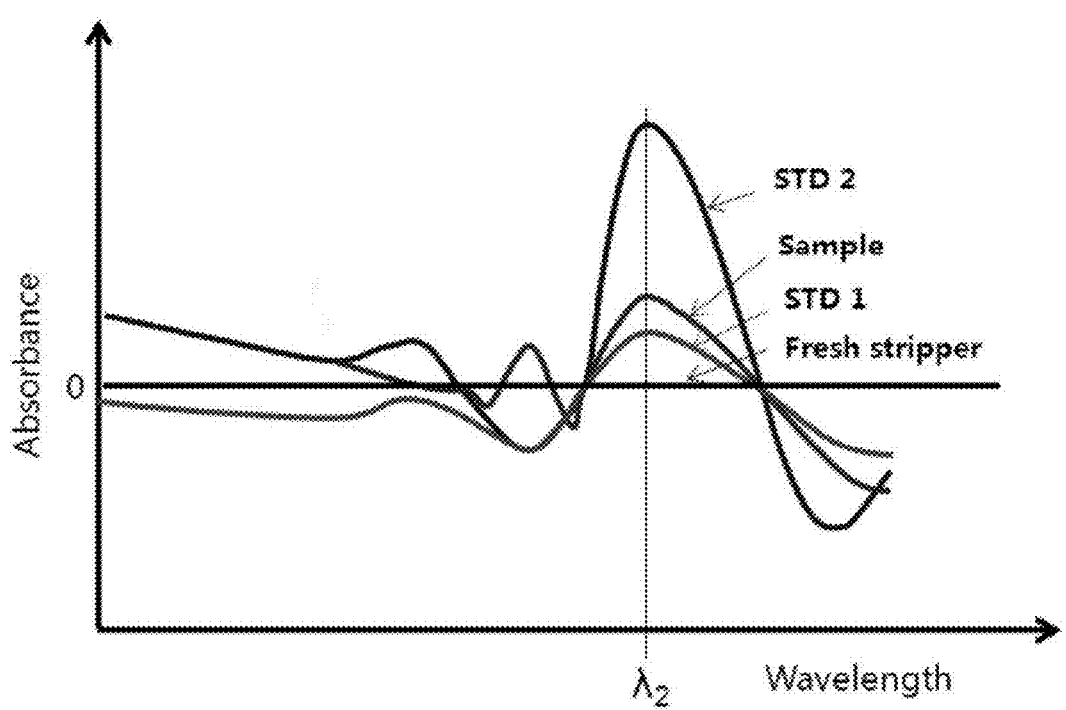
FIG. 3 is a schematic view illustrating that both the absorbance of the nth derivative curves of the nth derivative of the spectrum of the standard photoresist samples and the absorbance of the nth derivative curves of the nth derivative of the spectrum of the test photoresist sample at the second wavelength λ2 are at respective peaks in another embodiment of the present invention.
Figure 4:
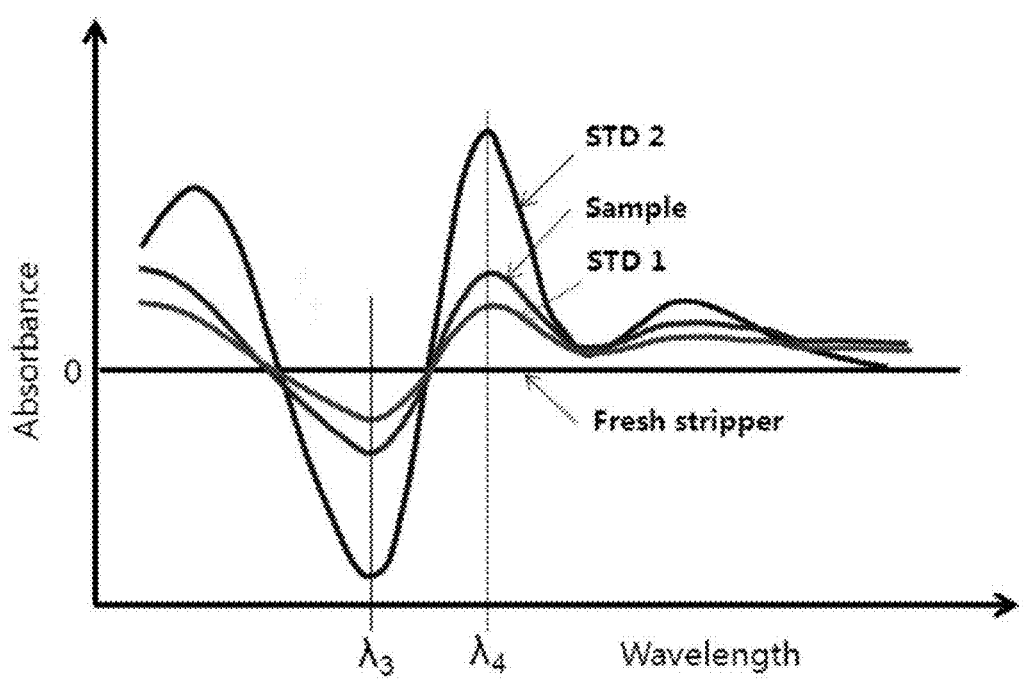
FIG. 4 is a schematic view illustrating that both the absorbance of the nth derivative curves of the nth derivative of the spectrum of the standard photoresist samples and the absorbance of the nth derivative curves of the nth derivative of the spectrum of the test photoresist samples at the third wavelength λ3 are at respective troughs, and both the absorbance of the nth derivative curves of the nth derivative of the spectrum of the standard photoresist samples and the absorbance of the nth derivative curves of the nth derivative of the spectrum of the test photoresist samples at the fourth wavelength λ4 are at respective peaks in yet another embodiment of the present invention.
Figure 5:
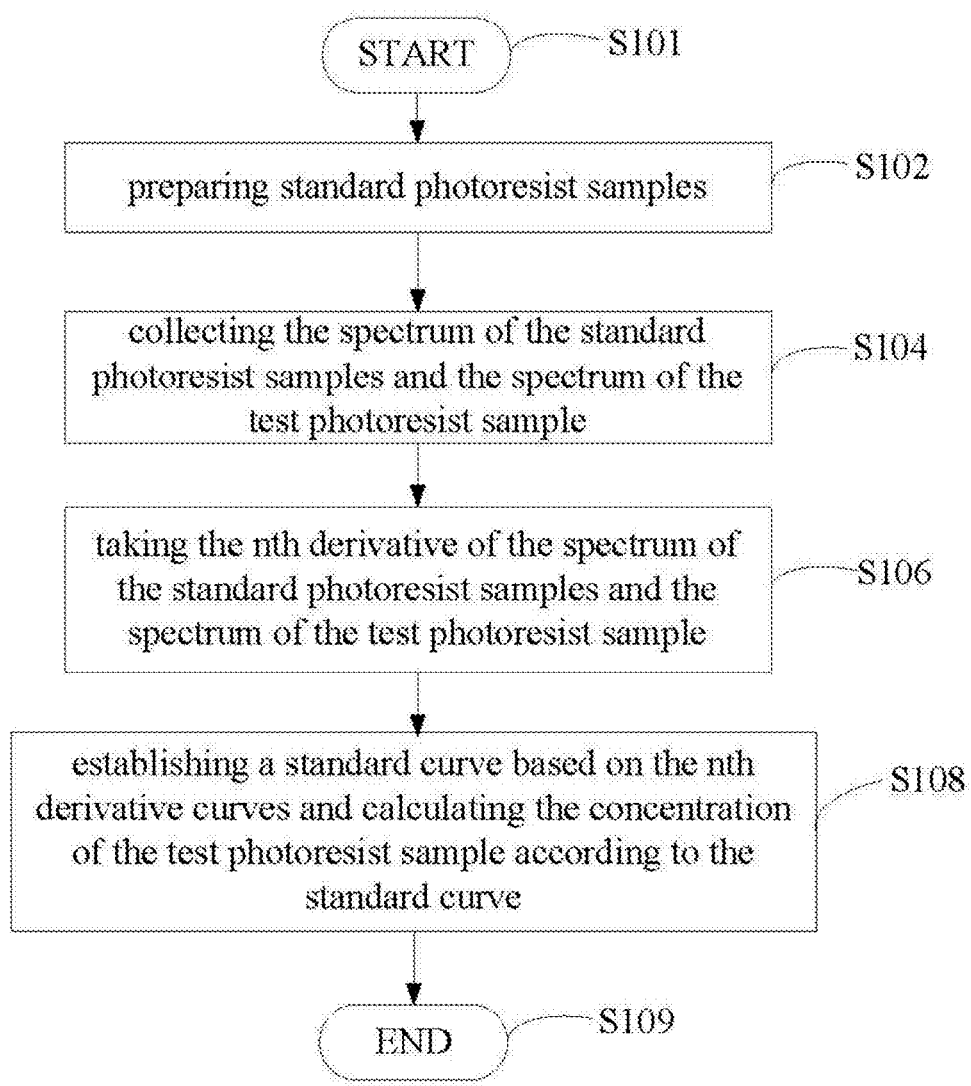
FIG. 5 is a flowchart of the method for measuring the concentration of a photoresist in a stripping liquid according to yet another embodiment of the present invention.

In step S106, the nth derivative of the spectrum of the stripping liquid, the spectrum of the standard photoresist samples and the spectrum of the test photoresist sample are taken wherein n is 1, 2, 3 or 4, and storing the nth derivative curves of the nth derivative of the spectrum of the stripping liquid, the spectrum of the standard photoresist samples and the spectrum of the test photoresist sample. The nth derivative of the spectrum of the stripping liquid, the spectrum of the standard photoresist samples and the spectrum of the test photoresist sample maybe taken by a operation software or drawing software. In FIG. 2, FIG. 3 and FIG. 4, the reference mark Fresh stripper means the nth derivative curves of the nth derivative of the spectrum of the stripping liquid, the reference mark Sample means the nth derivative curves of the nth derivative of the spectrum of the test photoresist sample, the reference mark STD 1 means the nth derivative curves of the nth derivative of the spectrum of the first standard photoresist sample, the reference mark STD 2 means the nth derivative curves of the nth derivative of the spectrum of the second standard photoresist sample.

In step S108, if the absorbance of the nth derivative curves of the nth derivative of the spectrum of the stripping liquid at a first wavelength λ1 is zero, and both the absorbance of the nth derivative curves of the nth derivative of the spectrum of the standard photoresist samples and the absorbance of the nth derivative curves of the nth derivative of the spectrum of the test photoresist sample at the first wavelength $\lambda 1$ are at respective troughs, then establishing the standard curve based on the respective troughs and the concentration of the photoresist of the standard photoresist samples.

In step S108, if the absorbance of the nth derivative curves of the nth derivative of the spectrum of the stripping liquid at a second wavelength $\lambda 2$ is zero, and both the absorbance of the nth derivative curves of the nth derivative of the spectrum of the standard photoresist samples and the absorbance of the nth derivative curves of the nth derivative of the spectrum of the test photoresist sample at the second wavelength $\lambda 2$ are at respective peaks, then establishing the standard curve based on the respective peaks and the concentration of the photoresist of the standard photoresist samples.

In step S108, if the absorbance of the nth derivative curves of the nth derivative of the spectrum of the stripping liquid between a third wavelength $\lambda 3$ and a fourth wavelength $\lambda 4$ is zero, both the absorbance of the nth derivative curves of the nth derivative of the spectrum of the standard photoresist samples and the absorbance of the nth derivative curves of the nth derivative of the spectrum of the test photoresist samples at the third wavelength $\lambda 3$ are at respective troughs, and both the absorbance of the nth derivative curves of the nth derivative of the spectrum of the standard photoresist samples and the absorbance of the nth derivative curves of the nth derivative of the spectrum of the test photoresist samples at the fourth wavelength $\lambda 4$ are at respective peaks, then establishing the standard curve based on the difference of the absorbance between the third wavelength $\lambda 3$ and the fourth wavelength $\lambda 4$ and the concentration of the photoresist of the standard photoresist samples.

The concentration of a photoresist in a stripping liquid can be measured accurately according to the standard curve. The standard curve is usually a straight line. By this way, the concentration of a photoresist in a stripping liquid can be obtained visually and directly. Thus, the time of the exchange of stripping liquid can be known in practical photo lithography of TFT array process. The life span of the stripping liquid can be extended. The method for measuring the concentration of a photoresist in a stripping liquid according to the present invention may be widely used in TFT technical field.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for measuring the concentration of a photoresist in a stripping liquid, the method for measuring the concentration of a photoresist in a stripping liquid comprising the steps of:
   S102: preparing standard photoresist samples;
   S104: collecting the spectrum of the standard photoresist samples and the spectrum of a test photoresist sample; and
   S106: taking the nth derivative of the spectrum of the standard photoresist samples and the spectrum of the test photoresist sample, wherein n is an integer equal to or greater than 1, and storing the nth derivative curves of the nth derivative of the spectrum of the standard photoresist samples and the spectrum of the test photoresist sample;
   S108: establishing a standard curve based on the nth derivative curves and calculating the concentration of the test photoresist sample;
   wherein the step S104 comprises the steps of:
   solvent preparing step: selecting a solvent as a reference solution;
   the spectrum of the stripping liquid collecting step: diluting the stripping liquid with the reference solution, collecting the spectrum of the striping liquid in the predetermined wavelength;
   the spectrum of the standard photoresist samples collecting step: diluting a plurality of standard photoresist samples with the reference solution, collecting the spectrum of the plurality of standard photoresist samples in the predetermined wavelength;
   the spectrum of the test photoresist sample collecting step: diluting the test photoresist sample with the reference solution, collecting the spectrum of the test photoresist sample in the predetermined wavelength, wherein in step S106, taking the nth derivative of the spectrum of the stripping liquid, the spectrum of the standard photoresist samples and the spectrum of the test photoresist sample, wherein n is 1, 2, 3 or 4, and storing the nth derivative curves of the nth derivative of the spectrum of the stripping liquid, the spectrum of the standard photoresist samples and the spectrum of the test photoresist sample, wherein in step S108, if the absorbance of the nth derivative curves of the nth derivative of the spectrum of the stripping liquid at a first wavelength is zero, and both the absorbance of the nth derivative curves of the nth derivative of the spectrum of the standard photoresist samples and the absorbance of the nth derivative curves of the nth derivative of the spectrum of the test photoresist sample at the first wavelength are at respective troughs, then establishing the standard curve based on the respective troughs and the concentration of the photoresist of the standard photoresist samples.

2. The method for measuring the concentration of a photoresist in a stripping liquid of claim 1, wherein in step S102, photoresist is coated on a glass, an exposure process, a developing process and an etching process are performed, and a stripping process is simulated in a beaker by stripping the photoresist with a target weight, such as to obtain the standard photoresist samples with target concentrations.

3. The method for measuring the concentration of a photoresist in a stripping liquid of claim 1, wherein in step S104, the spectrum of the standard photoresist samples and the spectrum of the test photoresist sample are collected by ultraviolet and visible spectrophotometer.

4. The method for measuring the concentration of a photoresist in a stripping liquid of claim 1, wherein in step S108, if the absorbance of the nth derivative curves of the nth derivative of the spectrum of the stripping liquid at a second wavelength is zero, and both the absorbance of the nth derivative curves of the nth derivative of the spectrum of the standard photoresist samples and the absorbance of the nth derivative curves of the nth derivative of the spectrum of the test photoresist sample at the second wavelength are at respective peaks, then establishing the standard curve based on the respective peaks and the concentration of the photoresist of the standard photoresist samples.

5. The method for measuring the concentration of a photoresist in a stripping liquid of claim 1, wherein in step S108, if the absorbance of the nth derivative curves of the nth derivative of the spectrum of the stripping liquid between a third wavelength and a fourth wavelength is zero, both the absorbance of the nth derivative curves of the nth derivative of the spectrum of the standard photoresist samples and the absorbance of the nth derivative curves of the nth derivative of the spectrum of the test photoresist samples at the third wavelength are at respective troughs, and both the absorbance of the nth derivative curves of the nth derivative of the spectrum of the standard photoresist samples and the absorbance of the nth derivative curves of the nth derivative of the spectrum of the test photoresist samples at the fourth wavelength are at respective peaks, then establishing the standard curve based on the difference of the absorbance between the third wavelength and the fourth wavelength and the concentration of the photoresist of the standard photoresist samples.

6. The method for measuring the concentration of a photoresist in a stripping liquid of claim 1, wherein the stripping liquid is organic amine stripping liquid.

7. The method for measuring the concentration of a photoresist in a stripping liquid of claim 4, wherein the stripping liquid is organic amine stripping liquid.

8. The method for measuring the concentration of a photoresist in a stripping liquid of claim 5, wherein the stripping liquid is organic amine stripping liquid.

9. The method for measuring the concentration of a photoresist in a stripping liquid of claim 1, wherein the photoresist is a phenolic resin positive type photoresist.

10. The method for measuring the concentration of a photoresist in a stripping liquid of claim 4, wherein the photoresist is a phenolic resin positive type photoresist.

11. The method for measuring the concentration of a photoresist in a stripping liquid of claim 5, wherein the photoresist is a phenolic resin positive type photoresist.

\* \* \* \* \*